United States Patent [19]

Devic et al.

[11] Patent Number: 5,352,827
[45] Date of Patent: Oct. 4, 1994

[54] SYNTHESIS OF ACYL CYANIDES IN A HYDROUS REACTION MEDIUM

[75] Inventors: Michel Devic; Pierre Tellier, both of Saint Foy les Lyon, France

[73] Assignee: Atochem, Puteau, France

[21] Appl. No.: 35,894

[22] Filed: Mar. 23, 1993

Related U.S. Application Data

[63] Continuation of Ser. No. 832,619, Feb. 11, 1992, abandoned, which is a continuation of Ser. No. 525,728, May 21, 1990, abandoned.

[30] Foreign Application Priority Data

May 19, 1989 [FR] France .................................. 89 06564

[51] Int. Cl.$^5$ .................... C07C 255/18; C07C 253/14
[52] U.S. Cl. ..................................................... 562/869
[58] Field of Search ............................................ 562/869

[56] References Cited

U.S. PATENT DOCUMENTS

| | | | |
|---|---|---|---|
| 4,113,773 | 9/1978 | Klenk et al. | 260/545 R |
| 4,143,068 | 3/1979 | Findeisen | 544/106 X |
| 4,144,269 | 3/1979 | Klenk et al. | 562/869 |
| 4,555,370 | 11/1985 | Klauke et al. | 260/545 R |

FOREIGN PATENT DOCUMENTS

| | | | |
|---|---|---|---|
| 0077661 | 5/1982 | Japan | 562/869 |
| 1520728 | 6/1977 | United Kingdom . | |

*Primary Examiner*—Joseph Paul Brust
*Attorney, Agent, or Firm*—Burns, Doane, Swecker & Mathis

[57] ABSTRACT

The acyl cyanides (nitriles) are prepared by reacting an acid halide with an alkali metal cyanide, in the presence of an alkylene oxide compound and a catalytically effective amount of water.

15 Claims, No Drawings

SYNTHESIS OF ACYL CYANIDES IN A HYDROUS REACTION MEDIUM

CROSS-REFERENCE TO COMPANION APPLICATION

This application is a continuation, of application Ser. No. 07/832,619, filed Feb. 11, 1992, now abandoned which is a continuation, of application Ser. No. 07/525,728, filed May 21, 1990.

BACKGROUND OF THE INVENTION

1. Field of the Invention

The present invention relates to the synthesis of acyl cyanides, and, more especially, to the synthesis of acyl cyanides by reacting acid halides with an alkali metal cyanide.

2. Description of the Prior Art

The acyl cyanides are known intermediates for a variety of organic syntheses, for example the production of herbicides.

FR 2,353,524 describes a synthesis of benzoyl cyanide $C_6H_5COCN$ by reacting benzoyl chloride with a molar excess of sodium cyanide in the presence of a nitrile of a carboxylic acid and copper cyanide.

FR 2,346,323 describes a similar, but much more general reaction, since it is applicable to an entire class of acyl cyanides, and entails reacting sodium cyanide with an excess of acid halide in the presence of copper or zinc cyanide.

The above processes present the disadvantage of requiring the presence of heavy metals and therefore mandate complicated treatments to avoid their presence in the reaction effluents.

Tetrahedron Letters (Pergamon Press) No. 26, pages 2275-2278 (1974) describes a process limited to the synthesis of benzoyl cyanide by reacting sodium cyanide with benzoyl chloride in solution in methylene chloride and in the presence of tetrabutylammonium bromide; the $C_6H_5COCN$ yield based on $C_6H_5COCl$ converted does not exceed 60%.

FR 2,364,894 describes the synthesis of $C_6H_5COCN$ by reacting $C_6H_5COCl$ with NaCN in a solvent in the presence of benzoic anhydride ($C_6H_5CO$—O—CO—$C_6H_5$) or of products which can generate benzoic anhydride under the reaction conditions. Example 1 of this patent was reproduced, namely, the reaction of benzoyl chloride, benzoic anhydride and sodium cyanide in xylene, at a temperature ranging from 140° to 145° C. for 8 hours, and a 51.2% molar yield of benzoyl cyanide was attained, based on the combined benzoic anhydride and benzoyl chloride converted, and a degree of conversion of 60.5%, based on the benzoyl chloride consumed. This examples was again repeated, except that moist sodium cyanide (0.4 g of water per 36.75 g of NaCN) was used; the yield increased from 51.2% to 88.2%.

Example 2 was also reproduced, namely, the reaction of benzoyl chloride, sodium cyanide and sodium benzoate in xylene at 135° C. The benzoate is presented to generate benzoic anhydride by reaction with benzoyl chloride. A degree of conversion of 23% of the benzoyl chloride consumed was determined and a 14.9% molar yield of benzoyl cyanide, relative to the benzoyl chloride consumed, instead of the reported 94%. This Example 2 was again repeated, except that moist sodium cyanide (0.5 g of water per 29.4 g of NaCN) was used; the degree of conversion increased from 23% to 85.7% and the yield from 14.9% to 67.8%.

The presence of water is therefore necessary to obtain an economically acceptable yield according to FR 2,364,894.

Example 3 of FR 2,364,894 relates to reacting benzoyl chloride, sodium cyanide and water in xylene at 135° C.

This is similar to Example 2, but the benzoate precursor of the anhydride is replaced with water. This Example 3 was reproduced and, after 2 hours of heating to 135° C., the yield did not exceed 60%.

SUMMARY OF THE INVENTION

Accordingly, a major object of the present invention is the provision of an improved process for the preparation of acyl cyanides in higher yields and at lower temperatures, which improved process is more reproducible, with greatly reduced reaction byproducts, than those processes to date characterizing the state of this art.

Briefly, the present invention features the synthesis of acyl cyanides of the formula (I):

in which R is either an alkyl radical having from 1 to 8 carbon atoms or a cycloalkyl radical having from 3 to 12 carbon atoms, or an aryl radical, or a heterocyclic radical which may be condensed with a benzene nucleus, all such radicals R either being unsubstituted or substituted, comprising reacting an acid halide of the formula (II):

in which R is as defined above and X is a halogen, with an alkali metal cyanide, in the presence of a compound containing alkylene oxide recurring units and also in the presence of catalytically effective amounts of water.

DETAILED DESCRIPTION OF THE PREFERRED EMBODIMENTS OF THE INVENTION

More particularly according to the present invention, the subject reaction is carried out according to the reaction scheme:

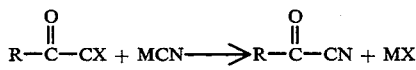

in which M is an alkali metal. It is advantageously carried out in a solvent medium. Upon completion of the reaction, the alkali metal halide and the optional excess of alkali metal cyanide are removed by filtration and washing with solvent. The pure acyl cyanide is recovered by distillation of the filtered reaction mixture.

The acid halides employed as starting materials have the formula (II). In this formula, R is preferably a linear or branched chain alkyl radical having from 1 to 4 carbons, or substituted such radicals; R also preferably is a cycloalkyl radical having 5 or 6 carbons, or substituted such radicals; R is also preferably a phenyl or naphthyl radical, or substituted such radicals; R also is preferably a five- or six-membered heterocyclic radical, or a substituted such heterocyclic radical.

In formula (II), X is advantageously chlorine or bromine.

The acid halide employed is generally added a little at a time to the reaction mixture with stirring, in pure form or diluted with the reaction solvent. The addition time period may range from a few minutes to several hours.

The preferred period of time is approximately 1 hour.

The alkali metal, preferably sodium or potassium, cyanide is employed in stoichiometric amount or else in excess thereof, in a proportion of 1 to 2 moles per mole of acid halide; the preferred amount ranges from 1 to 1.25 moles per mole of acid halide.

The reaction is advantageously carried out in the presence of an inert solvent.

Any solvent which does not react with the acid halide or with the alkali metal cyanide under the reaction conditions can be employed.

Exemplary of such solvents which are suitable for the reaction, the following are particularly representative:
(i) benzene-related hydrocarbons, such as benzene, toluene, xylene, chlorobenzene, and the like;
(ii) halogenated aliphatic hydrocarbons, such as trichloroethylene or tetrachloroethane;
(iii) ethers or esters which are inert under the reaction conditions.

The preferred solvents for the reaction are toluene and xylene.

The amount of solvent may vary over wide limits. From 150 to 500 ml per mole of acid halide is typically sufficient.

It is also within the scope of the invention to use a larger amount of solvent, but this would require distilling a larger amount to recover the acyl cyanide.

The reaction can be carried out at temperatures ranging from 60° to 150° C. The preferred temperature ranges from 90° to 120° C.

The reaction is advantageously carried out at atmospheric pressure, if the selected solvent permits such reaction condition. The reaction can also be carried out under inert gas pressure, or under solvent vapor pressure when the boiling point of the selected solvent is lower than the reaction temperature.

The reaction is very rapid and is, for example, complete after 15 to 30 minutes at 120° C. However, heating is continued for a period of time of 1 to 2 hours to remove any trace amounts of acid halide. The preferred reaction period is 2 hours at 95° C.

The compound containing alkylene oxide recurring units advantageously contains from 2 to 200 units selected from between ethylene oxide and propylene oxide.

It is, for example, a product containing one or more of the chains:

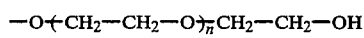

wherein the total number of the n or n's ranges from 2 to 200; exemplary thereof are:
(i) polyoxyethylenated alkylphenols:

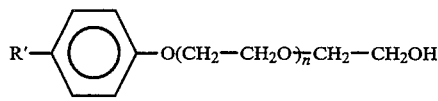

wherein R' is an alkyl radical having up to 20 carbon atoms, with R' being, for example, $C_8H_{17}$ or $C_9H_{19}$ or $C_{12}H_{17}$, and n ranges from 20 to 100;

(ii) polyoxyethylenated stearates:

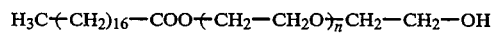

(iii) simple polyethylene glycols of the formula:

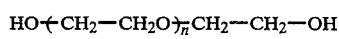

having a molecular weight ranging from 100 to 4,000.

Among such compounds comprising a number of polyethylenated recurring units, representative are the triglyceride derivatives of polyethylene glycols in which the total number of ethylene oxide units ranges from 20 to 150.

Products which are similar to the above compounds can also be used, in which the ethylene oxide unit is replaced by the propylene oxide unit or a mixture of ethylene oxide and propylene oxide units.

The amount of this product may range from 0.1 to 10 g per mole of acid halide, with the preferred amount ranging from 0.4 to 2 g.

The product is generally added to the reaction solvent, but it can also be added wholly or partly with the pure or solvent-diluted acid halide. Small amounts of water must be added to the reactants to provide a high yield and degree of conversion.

The amount of water which must be present during the reaction ranges from 0.2 to 2 g of water per mole of acid halide. The preferred amount of water ranges from 0.5 to 1 g of water per mole of acid halide.

The manner in which the water is introduced must be such as to ensure a good distribution thereof over the reactants.

In order to further illustrate the present invention and the advantages thereof, the following specific examples are given, it being understood that same are intended only as illustrative and in nowise limitative.

In said examples to follow, by "degree of conversion" is intended the amount of acid halide consumed relative to the initial amount thereof and by "yield" is intended the ratio of the number of moles of acyl cyanide produced to the number of moles of acid halide initially present.

EXAMPLE 1

36.75 g of anhydrous sodium cyanide (0.75 mol) and 0.4 g of water were introduced into a glass reactor fitted with a stirrer and a condenser, containing 150 cm³ of xylene and 0.5 g of the polyoxyethylenated nonylphenol of the formula:

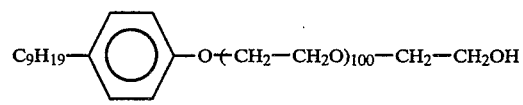

(marketed by GAF under the trademark Antarox CO 990).

70.3 g of benzoyl chloride (0.50 mol) were then introduced over 0.5 hours at 125° C. and the temperature was increased to 140° C. for 2 hours.

After cooling, the resulting inorganic precipitate (42.9 g) was filtered off and washed.

The filtrate was distilled and 60.05 g of pure benzoyl cyanide were collected, i.e., a yield of 91.6%.

EXAMPLE 2

24.5 g of sodium cyanide (0.5 mol) and 0.5 g of water were introduced into a glass reactor fitted with a stirrer and a condenser, containing:
(i) 150 cm$^3$ of xylene, and
(ii) 0.5 g of Antarox CO 990.

These materials were heated to 95° C. and 70.3 g of benzoyl chloride (0.5 mol) were introduced over 1 hour. The temperature was maintained at 95° C. for two hours and then, after cooling, the solids were filtered off and washed with xylene (29.2 g of inorganic precipitate).

A xylene solution having a weight of 231.4 g was obtained after filtration. Gas chromatography analysis with an internal standard evidenced 26.3% of benzoyl cyanide, i.e., a total amount of 60.85 g of pure benzoyl cyanide, corresponding to a yield of 92.8%.

EXAMPLE 3

The procedure of Example 2 was repeated, using:
(i) 150 cm$^3$ of xylene;
(ii) 0.5 g of Antarox CO 990;
(iii) 29.4 g of anhydrous sodium cyanide (0.6 mol)
(iv) 0.4 g of water;
(v) 70.3 g of benzoyl chloride (0.5 mol).

After reaction, a degree of conversion of 99% of the benzoyl chloride was obtained, and a yield, relative to the benzoyl chloride consumed, of 86.2%.

EXAMPLE 4 (not according to the invention)

The procedure of Example 3 was repeated, but the introduction of the water was omitted.

A degree of conversion of 32% and a chemical yield of 23.8% were obtained.

EXAMPLE 5 (not according to the invention)

The procedure of Example 3 was repeated, but the introduction of polyoxyethylene derivative (Antarox CO 990) was omitted.

A degree of conversion of 79% and a 70.2% yield were obtained.

This example was similar to Example 3 of FR 2,364,894.

EXAMPLE 6

The procedure of Example 3 was repeated, except that the Antarox CO 990 was replaced with Antarox CO 850 of the formula:

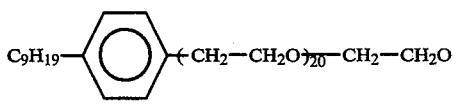

A degree of conversion of 99% and an 81.5% yield were obtained.

EXAMPLE 7

The procedure of Example 3 was repeated, except that the Antarox CO 990 was replaced with a stearate polyethoxylated with 100 ethylene oxide units, marketed by ICI under the trademark Brij 700 and having the formula:

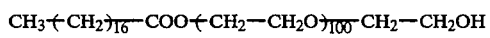

A degree of conversion of 99% and an 84.6% yield were obtained.

EXAMPLE 8

The procedure of Example 3 was repeated, except that the Antarox CO 990 was replaced with a triglyceride of polyoxyethylene glycol having 150 ethylene oxide units, marketed by Atlas under the trademark G 1295.

The degree of conversion was 98.8% and the yield was 83.3%.

EXAMPLE 9

The procedure of Example 3 was repeated, except that the Antarox CO 990 was replaced with a mixed polyoxyethylene and polyoxypropylene monostearate (Atlas G 2162) containing 25 oxyethylene units.

A degree of conversion of 100% and an 84% yield were obtained.

EXAMPLE 10

The procedure of Example 7 was repeated, but instead of filtering after reaction, the crude mixture containing the inorganic salt was distilled.

A residue of inorganic salts and of inorganic products was obtained, weighing 43 g, and 260 g of a distillate containing 55.4 g of benzoyl cyanide, i.e., a yield of 84.5%.

EXAMPLE 11

The procedure of Example 3 was repeated, except that the xylene was replaced with an equal volume of toluene.

A degree of conversion of 98.6% and an 83.2% yield were obtained.

EXAMPLE 12

The procedure of Example 3 was repeated, except that the addition and the heating were carried out at a temperature of 105° C. instead of 95° C.

A degree of conversion of 99.1% and an 83.8% yield were obtained.

EXAMPLE 13

Into a 250-ml round bottomed flask were introduced:
(i) 14.7 g of sodium cyanide;
(ii) 0.2 g of water (0.011 mol);
(iii) 80 g of xylene;
(iv) 0.2 g of Antarox 990.

35.15 g of benzoyl chloride were introduced over one hour at 95° C. The reaction was permitted to continue for another 3 hours at 98° C.

The precipitate was removed by filtration and washing with xylene. 15.4 g of salt and 164 g of organic solution were thus collected.

Quantitative analysis of the organic solution by vapor phase chromatography evidenced that it contained 28.7 g of benzoyl cyanide, which represents an 87.6% yield relative to the benzoyl chloride consumed. The degree of conversion of benzoyl chloride was 99%.

EXAMPLE 14 (COMPARATIVE)

The procedure of Example 13 was repeated, except that the water was replaced with 2.5 g of benzoic anhydride (0.011 mol).

The degree of conversion of benzoyl chloride was only 19% and the benzoyl cyanide yield relative to the benzoyl chloride consumed was only 9.7%.

EXAMPLE 15

The procedure of Example 13 was repeated, except that the Antarox was replaced with 0.2 g of polyethylene glycol of average molecular weight of 200.

After the introduction of benzoyl chloride, the mixture was maintained at 98° C. for 2 hours and at 115° C. for 2 hours. The solution obtained after the salt separation contained 29.3 g of benzoyl cyanide which corresponds to an 89.5% yield relative to the benzoyl chloride consumed. The degree of conversion of benzoyl chloride was 98%.

EXAMPLE 16

The procedure of Example 15 was repeated, using a polyethylene glycol of average molecular weight of 3,400.

The degree of conversion of benzoyl chloride was 100% and the benzoyl cyanide yield was 91.2% relative to the benzoyl chloride consumed.

EXAMPLE 17

The procedure of Example 13 was repeated, but with all of the amounts being multiplied by 8. After the introduction of benzoyl chloride, the mixture was maintained at 98° C. for another 2 hours and at 115° C. for 2 hours.

After the separation of salt, the solution was distilled. 234.4 g of benzoyl cyanide were collected, which represents an 89.4% yield relative to the benzoyl chloride consumed. The degree of conversion was 100%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an acyl cyanide having the formula (I):

$$\underset{R-C-CN}{\overset{\overset{\displaystyle O}{\|}}{}} \quad (I)$$

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

$$\underset{R-C-X}{\overset{\overset{\displaystyle O}{\|}}{}} \quad (II)$$

in which R is as defined above and X is a halogen atom, with an alkali metal cyanide in the presence of an acyl cyanide yield enhancing amount of a poly(alkylene oxide) compound and a catalytically effective amount of water, wherein the reactants are selected and used in amounts and under conditions which result in the production of said acyl cyanide.

2. The process as defined by claim 1, carried out in the presence of a solvent medium.

3. The process as defined by claim 1, wherein the amount of alkali metal cyanide ranges from 1 to 2 moles per mole of acid halide.

4. The process as defined by claim 3, said amount of alkali metal cyanide ranging from 1 to 1.25 moles per mole of acid halide.

5. The process as defined by claim 1, said alkali metal cyanide comprising sodium cyanide.

6. The process as defined by claim 2, said solvent medium comprising xylene or toluene.

7. The process as defined by claim 1, wherein the amount of said alkylene oxide compound ranges from 0.1 to 10 g per mole of acid halide.

8. The process as defined by claim 7, said amount of alkylene oxide compound ranging from 0.4 to 2 g per mole of acid halide.

9. The process as defined by claim 1, said catalytically effective amount of water ranging from 0.2 to 2 g per mole of acid halide.

10. The process as defined by claim 9, said catalytically effective amount of water ranging from 0.5 to 1 g per mole of acid halide.

11. The process as defined by claim 1, said acid halide comprising benzoyl chloride.

12. The process as defined by claim 2, wherein the amount of solvent ranges from 150 to 500 ml per mole of acid halide.

13. A process for the preparation of an acyl cyanide having the formula (I):

$$\underset{R-C-CN}{\overset{\overset{\displaystyle O}{\|}}{}} \quad (I)$$

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

$$\underset{R-C-X}{\overset{\overset{\displaystyle O}{\|}}{}} \quad (II)$$

in which R is as defined above and X is a halogen atom, with an alkali metal cyanide, in the presence of an acyl cyanide yield enhancing amount of a poly(alkylene oxide) compound containing 2 to 200 ethylene oxide or propylene oxide recurring units, or combination thereof and a catalytically effective amount of water, wherein reactants are selected and used in amounts and under conditions which result in the production of said acyl cyanide.

14. A process for the preparation of an acyl cyanide having the formula (I):

$$R-\overset{\overset{O}{\|}}{C}-CN \quad (I)$$

in which R is an alkyl radical having from 1 to 8 carbon atoms, a cycloalkyl radical having from 3 to 12 carbon atoms, an aryl radical, a heterocyclic radical optionally condensed with a benzene nucleus, or substituted such radicals, comprising reacting in the liquid phase an acid halide of the formula (II):

$$R-\overset{\overset{O}{\|}}{C}-X \quad (II)$$

in which R is as defined above and X is a halogen atom, with an alkali metal cyanide, in the presence of an acyl yield enhancing amount of a poly(alkylene oxide) compound containing one or more of the chains: $-O-(CH_2-CH_2-O)n-CH_2-CH_2-OH$ where n ranges from 2 to 200, and a catalytically effective amount of water, wherein the reactants are selected and used in amounts and under conditions which result in the production of said acyl cyanide.

15. The process as defined in claim 1, wherein said acyl halide is reacted with said alkali metal cyanide in the further presence of an inert solvent wherein said inert solvent is not said alkylene oxide compound.

* * * * *